US00PP28853P3

(12) United States Plant Patent
White

(10) Patent No.: US PP28,853 P3
(45) Date of Patent: Jan. 9, 2018

(54) PEAR TREE NAMED 'PREMP003'

(50) Latin Name: ***Pyrus bretschneideri*×*Pyrus communis***
Varietal Denomination: PremP003

(71) Applicant: Allan G. White, Havelock North (NZ)

(72) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 14/544,403

(22) Filed: Dec. 31, 2014

(65) Prior Publication Data

US 2015/0195971 P1 Jul. 9, 2015

Related U.S. Application Data

(60) Provisional application No. 61/924,150, filed on Jan. 6, 2014.

(51) Int. Cl.
*A01H 5/08* (2006.01)

(52) U.S. Cl.
USPC ..... Plt./176

(58) Field of Classification Search
USPC ..... Plt./176
See application file for complete search history.

*Primary Examiner* — Keith Robinson
(74) *Attorney, Agent, or Firm* — Michelle Bos Legal LLC

(57) ABSTRACT

A new and distinct pear tree named 'PremP003' is disclosed. The new pear tree is notable for the size and quality of its fruit.

2 Drawing Sheets

Latin name of the genus and species of the plant claimed: *Pyrus bretschneideri*×*Pyrus communis*.

Variety denomination: 'PremP003'.

BRIEF DESCRIPTION OF THE PHOTOGRAPHS

Figure 1:
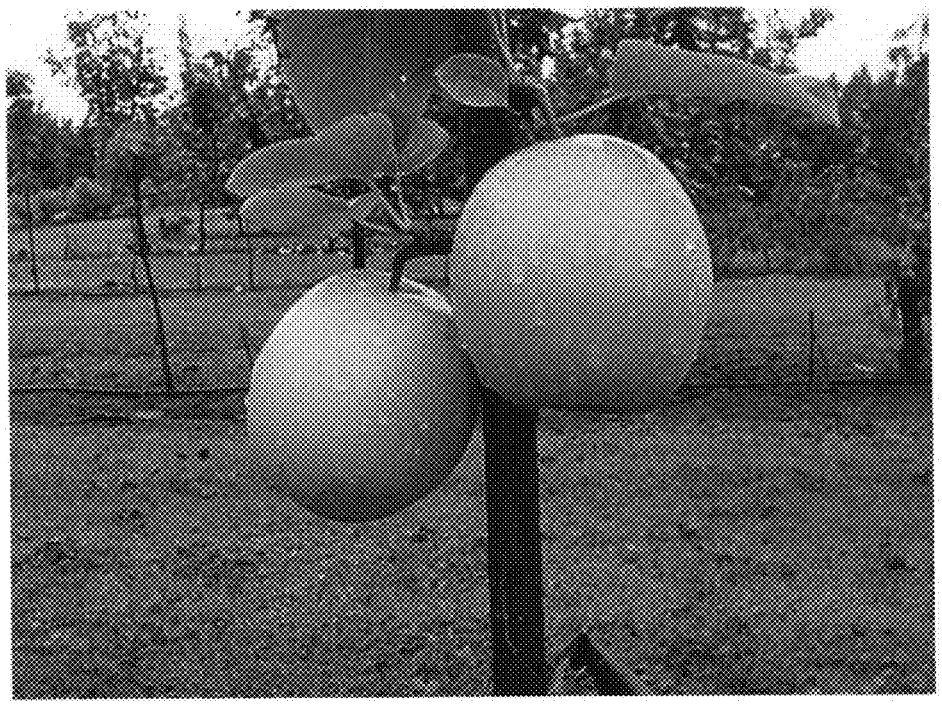
Figure 2:
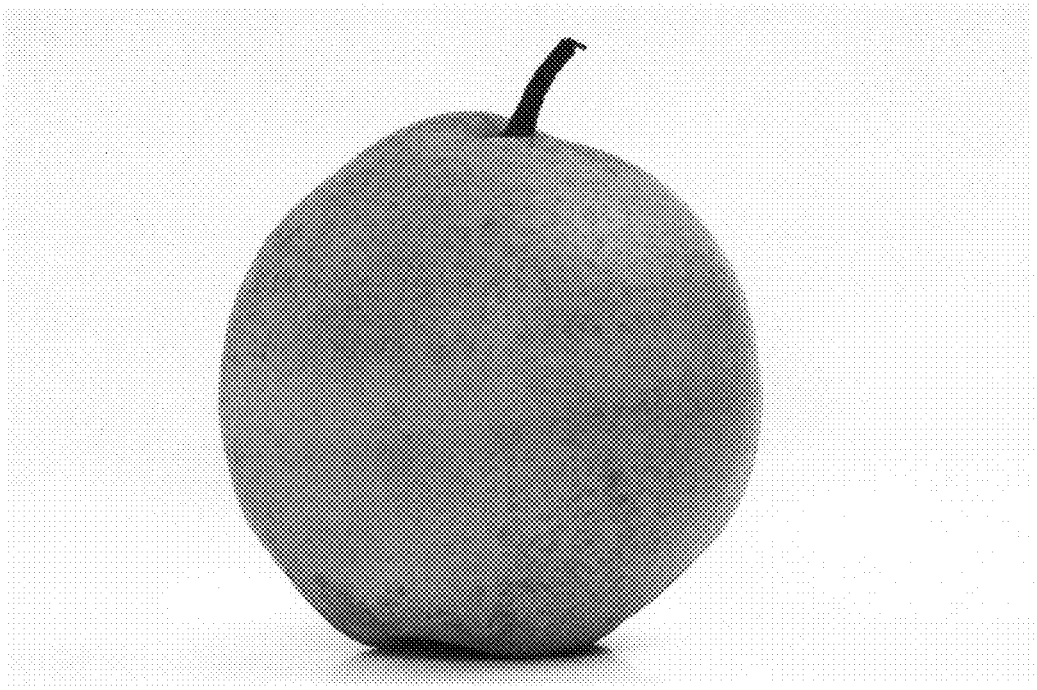

FIGS. 1 and 2 show the fruit of a 'PremP003' pear tree at harvest time.

BRIEF DESCRIPTION OF THE VARIETY

The new variety of pear tree 'PremP003' was created in the course of a planned breeding program carried out at Motueka, New Zealand. 'PremP003' originated as a result of a controlled cross of 'Max Red Bartlett' (seed parent, U.S. Plant Pat. No. 741) and 'Snowflake' (pollen parent, not patented) in 1989. 'PremP003' was selected in 1996 as a single plant from among a population of seedlings derived from the parents, and was selected for its fruit size and quality of fruit. It is distinguished from its parents by its shape and color. 'Max Red Bartlett' fruit is pyriform in shape with high coverage of red skin color compared to 'PremP003' which has no red skin color and is substantially globose in shape. Fruit of 'PremP003' has less prominent lenticels than 'Snowflake'. 'PremP003' is distinguishable from related variety 'PremP027' (U.S. Ser. No. 14/544,401, pending) by its later harvest maturity, which about three weeks after 'PremP027'.

Asexual propagation by budding was first carried out in Havelock North, New Zealand. The variety has since been observed over a number of asexually propagated generations, and has been found to remain true to type.

DETAILED BOTANICAL DESCRIPTION OF THE VARIETY

The following detailed botanical description is based on observations made during the 2013 growing season at Parker, Wash. on 5 year old trees. All colors are described according to The Royal Horticultural Society Colour Chart as published in 2001. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:
- *Vigor*.—Medium.
- *Habit*.—Upright.
- *Branching*.—Medium.
- *Size*.—Height 9 feet, spread 1.5 feet.
- *Trunk*.—Diameter at 5 cm above graft union 7 cm.
- *Bark texture*.—Smooth.

Branch:
- *Size*.—Diameter 7 cm at 74 cm above soil.
- *Crotch angle relative to trunk*.—80°.

Dormant one-year-old shoot:
- *Size*.—Diameter 3 cm, length 13 cm.
- *Color*.—Yellow-green 152B.
- *Internode length*.—5 to 6 cm.
- *Lenticels*.—Quantity 8 per square inch, color white N155C, diameter 1 cm.
- *Vegetative bud*.—Acute, slightly held out.
- *Bark texture*.—Smooth.

Growing young shoot:
- *Anthocyanin coloration of growing tip*.—Medium.
- *Pubescence of upper third of shoot*.—Weak.

Flowers:
- *Bud*.—Quantity per spur 8 to 9.
- *Bud size*.—Diameter 1 cm, length 1.5 cm, color red-purple 65B, pink on edges.
- *Petals*.—5 per flower, margins smooth to ruffled, touching.

*Petal size*.—Diameter 1.5 cm, length 2 cm.
*Petal shape*.—Rounded.
*Petal color*.—White 155C.
*Petal texture*.—Smooth upper and lower surface.
*Sepals*.—Quantity per flower 5, diameter 0.2 cm, length 0.5 cm.
*Pedicel*.—Diameter 0.1 cm, length 2.5 cm, color yellow-green 145A.
*Anthers*.—Quantity per flower 10, length 0.1 cm, pollen color yellow 4C.
*Stigma*.—Size 0.1 cm, color brown 200D.
*Style*.—Length 0.4 cm, color yellow 4C.
*Ovary*.—Size 0.3 cm, color yellow-green 151B.
*Bloom period*.—First bloom April 15, full bloom April 20 in Parker, Wash.

Leaf:
*Attitude in relation to shoot*.—Upward.
*Blade margin*.—Serrulate.
*Size*.—Length 8 cm, width 5 cm.
*Shape*.—Ovate with rounded base, acuminate tip.
*Upper surface*.—Color yellow-green 144A, texture smooth.
*Lower surface*.—Color yellow-green 146D, texture smooth.

Petiole:
*Length*.—5 cm.
*Diameter*.—0.1 cm.
*Color*.—Yellow-green 146D.
*Stipules*.—Present.

Fruit:
*Size*.—Diameter 8.9 cm, length 10 cm.
*Position of maximum diameter*.—Middle.
*Profile of sides*.—Convex; Ribbing absent.
*Size of eye*.—3 cm.
*Depth of eye basin*.—1 cm.
*Width of eye basin*.—1.5 cm.
*Relief of area around eye*.—Smooth.
*Stalk*.—Length 5.5 cm, width at limb attachment 0.5 cm, color greyed-orange N167B.
*Depth of stalk cavity*.—0.3 cm.
*Attitude of stalk in relation to fruit*.—Oblique.
*Width of stalk cavity*.—0.5 cm.
*Size of lenticels*.—0.1 cm.
*Color of lenticels*.—Brown 200D.
*Ground color of skin*.—Yellow-green 153D.
*Overcolor*.—Absent.
*Quantity per cluster*.—3 to 4.
*Flesh texture*.—Crisp and juicy.
*Flesh color*.—White 155B.
*Quantity of seeds*.—6.
*Seed width*.—0.4 cm.
*Seed length*.—1 cm.
*Seed shape*.—Ovate.
*Seed color*.—Brown 200A.
*Harvest date*.—Mid-season (mid-September).

Use: Fresh Market.

I claim:

1. I claim a new and distinct pear tree substantially as shown and described herein.

* * * * *